United States Patent
Thfoin et al.

(10) Patent No.: US 9,433,568 B2
(45) Date of Patent: Sep. 6, 2016

(54) COLOURED FRAGRANCING COMPOSITION WITH NO ALKYL DIPHENYLACRYLATE THAT CONTAINS A DERIVATIVE OF BENZYLIDENE CAMPHOR CONTAINING A SULPHONIC FUNCTION OR A BENZOTRIAZOLE SILICONE

(75) Inventors: Willy Thfoin, Massy (FR); Boris Grimal, L'hay-les-Roses (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/949,406

(22) Filed: Nov. 18, 2010

(65) Prior Publication Data

US 2012/0148508 A1    Jun. 14, 2012

Related U.S. Application Data

(60) Provisional application No. 61/265,593, filed on Dec. 1, 2009, provisional application No. 61/265,583, filed on Dec. 1, 2009.

(30) Foreign Application Priority Data

Nov. 19, 2009   (FR) ...................................... 09 58181
Nov. 19, 2009   (FR) ...................................... 09 58183

(51) Int. Cl.
*A61K 8/58*   (2006.01)
*A61K 8/46*   (2006.01)
*A61Q 13/00*   (2006.01)

(52) U.S. Cl.
CPC ............... *A61K 8/585* (2013.01); *A61K 8/466* (2013.01); *A61Q 13/00* (2013.01); *A61K 2800/42* (2013.01); *A61K 2800/522* (2013.01)

(58) Field of Classification Search
CPC .. A61Q 19/00; A61Q 13/00; A61K 2800/10; A61K 2800/42; A61K 2800/52; A61K 8/466; A61K 8/585
See application file for complete search history.

(56) References Cited

U.S. PATENT DOCUMENTS

| | | | | |
|---|---|---|---|---|
| 3,271,339 A * | 9/1966 | Bonvicini et al. | ............... | 524/91 |
| 4,327,031 A * | 4/1982 | Bouillon et al. | ............... | 556/120 |
| 5,549,886 A * | 8/1996 | Grollier | ........................... | 424/59 |
| 5,643,557 A * | 7/1997 | Eteve et al. | .................... | 424/60 |
| 5,658,555 A * | 8/1997 | Ascione et al. | ................. | 424/59 |
| 5,788,973 A * | 8/1998 | Ascione | ........................ | 424/401 |
| 2002/0081271 A1 * | 6/2002 | Martin et al. | .................... | 424/59 |
| 2003/0099679 A1 * | 5/2003 | Gonzalez et al. | ............. | 424/405 |
| 2005/0129635 A1 * | 6/2005 | Erdelmeier et al. | ............ | 424/59 |
| 2005/0244349 A1 * | 11/2005 | Chaudhuri et al. | ............. | 424/59 |
| 2008/0003247 A1 * | 1/2008 | Shick et al. | .................. | 424/401 |

FOREIGN PATENT DOCUMENTS

FR    2818143 A1 *   6/2002
JP    2002087948 A *   3/2002

OTHER PUBLICATIONS

Candau, FR 2818143 A1, Jun. 2002, Derwent English abstract.*
Nakamura, JP 2002087948 A, Mar. 2002, Derwent English abstract.*

* cited by examiner

*Primary Examiner* — Brian-Yong Kwon
*Assistant Examiner* — Mark V Stevens
(74) *Attorney, Agent, or Firm* — Polsinelli PC

(57) ABSTRACT

A colored fragrancing composition is provided that comprises, in a cosmetically acceptable medium: a) at least 2% by weight of a fragrancing substance relative to the total weight of the composition; b) at least one derivative of benzylidene camphor containing a sulphonic function or a benzotriazole silicone of particular formula (1) that will be defined below in detail; c) at least one dye that is soluble in said medium; said composition not containing an alkyl β,β'-diphenylacrylate compound or an alkyl α-cyano-β,β'-diphenylacrylate compound. Also provided is a cosmetic method for fragrancing human keratin substances and in particular the skin, lips and integuments, comprising the application to the keratin substances of the composition defined previously.

13 Claims, No Drawings

COLOURED FRAGRANCING COMPOSITION WITH NO ALKYL DIPHENYLACRYLATE THAT CONTAINS A DERIVATIVE OF BENZYLIDENE CAMPHOR CONTAINING A SULPHONIC FUNCTION OR A BENZOTRIAZOLE SILICONE

CROSS REFERENCE TO RELATED APPLICATIONS

This application claims priority under 35 U.S.C. §119(a) to Patent Application No. 0958181 filed in France on Nov. 19, 2009 and Patent Application No. 0958153 filed in France on Nov. 19, 2009, and this application claims priority under 35 U.S.C. §119(e) to U.S. Provisional Application No. 61/265,593 filed on Dec. 1, 2009 and U.S. Provisional Application No. 61/265,583 filed on Dec. 1, 2009, the entire contents of which are hereby incorporated by reference.

The invention relates to a coloured fragrancing composition comprising, in a cosmetically acceptable medium:
a) at least 2% by weight of a fragrancing substance relative to the total weight of the composition;
b) at least one derivative of benzylidene camphor containing a sulphonic function or a benzotriazole silicone of particular formula (1) that will be defined below in detail;
c) at least one dye that is soluble in said medium; said composition not containing an alkyl β,β'-diphenylacrylate or alkyl α-cyano-β,β'-diphenylacrylate compound.

It is known that a fragrance is the combination of various odorous substances that evaporate at different times. Each fragrance exhibits what is known as a "top note" which is the odour which first diffuses when the fragrance is applied or when the receptacle containing it is opened, a "heart or middle note" which corresponds to the complete fragrance (emitted for several hours after the "top note") and a "base note" which is the most persistent odour (emitted for several hours after the "heart note"). The persistence of the heart note and of the base note corresponds to the staying power of the fragrance.

Human beings have always sought to fragrance themselves and to fragrance the articles which surround them or the places in which they find themselves, both to mask strong and/or unpleasant odours and to give a pleasant odour.

Fragrance is routinely incorporated into a certain number of products or compositions, in particular cosmetic or dermatological compositions such as eaux fraiche (splash), eaux de toilette, eaux de parfum, aftershave lotions and skincare waters. For reasons relating to aesthetics and manufacturing cost, the concentrate of fragrances is coloured by adding an effective amount of dye that is soluble in the carrier of the formulation (generally alcoholic or aqueous/alcoholic) rather than tinting or lacquering the bottle which is a more costly industrial operation. The colour developed in these fragrance formulations must remain stable both over time and when exposed to light. Generally, a screening system and/or an antioxidant system is added.

In application EP 1 897 592, coloured fragrancing compositions are proposed that comprise, as a stabilizing system, at least. 0.2% by weight relative to the total weight of the composition of at least one alkyl β,β'-diphenylacrylate or alkyl α-cyano-β,β'-diphenylacrylate compound such as octocrylene and at least one organic UV-A screening agent that is soluble in said medium.

However, the use of an alkyl β,β'-diphenylacrylate compound or of an alkyl α-cyano-β,β'-diphenylacrylate compound such as octocrylene and of a UVA screening agent had a tendency, on the one hand, to produce unforeseeable recrystallizations depending on the fragrance concentrate used. On the other hand, the applicant discovered during its research that an alkyl β,β'-diphenylacrylate compound or an alkyl α-cyano-β,β'-diphenylacrylate compound such as octocrylene inhibited the stabilization of the colour in particular in the field of yellows and that of violets.

In application. WO 2005/042828, coloured fragrancing compositions were proposed comprising, as a stabilizing system, a derivative of piperidinol (i.e. tris(tetramethylhydroxypiperidinol) citrate—TINOGUARD Q) combined with an organic UV screening agent chosen from dibenzoylmethane derivatives, cinnamates, camphor derivatives and s-triazines. Example 6 describes, in particular, an eau de toilette comprising a fragrance, a dye, 0.1% of a mixture of butyl methoxydibenzoylmethane and octocrylene, a stabilizer of piperidinol type.

However, these piperidinol derivatives have the drawback of generating a yellowing of the eaux de toilette and also an unwanted odour.

In application WO 00/25370, coloured eaux de toilette are recommended that are stabilized by one particular benzotriazole compound and/or one particular traizine such as, for example, sodium benzotriazolyl butylphenol sulphonate such as the product sold under the name TINOGUARD HS by the company Ciba-Geigy; benzotriazolyl dodecyl p-cresol such as the product sold under the name TINOGUARD TL by the company Ciba-Geigy, the product sold under the trade name CIBAFAST H LIQUID by the company Ciba-Geigy, bumetrizole such as the product sold under the name TINOGUARD AS by the company Ciba-Geigy. In applications WO 09/059872 and FR 2923386, the use of one particular benzotriazole compound, especially bumetrizole (TINOGUARD AS) was proposed in combination with other particular screening agents such as a dibenzoylmethane derivative with an alkyl β,β'-diphenylacrylate or alkyl α-cyano-β,β'-diphenylacrylate compound.

However, these benzotriazole compounds, in particular bumetrizole (TINOGUARD AS) are not easy to dissolve in eaux de toilette, have a tendency to recrystallize over time, and in addition have a mediocre stabilizing power.

In patent applications EP 1 994 921, FR 2 916 347, FR 2 916 348 and FR 2 916 349 the use of a UV screening agent of the aminobenzophenone type such as n-hexyl. 2-(4-diethylamino-2-hydroxybenzoyi)benzoate sold under the trade name UVINUL A+ with other particular screening agents has also been proposed in order to stabilize the colour of the eaux de toilette. However, aminobenzophenone screening agents such as UVINUL, A+ introduce a yellow colour which is undesirable for fragranced formulations of pale colour other than yellow.

There remains the need for coloured fragrancing products that do not exhibit the disadvantages of the prior art products, and especially the need for coloured fragrancing products the colour of which remains stable over time and under the effects of light.

The applicant has surprisingly discovered that this objective could be achieved by using a coloured fragrancing composition comprising, in a cosmetically acceptable medium:
a) at least 2% by weight of a fragrancing substance relative to the total weight of the composition;
b) at least one derivative of benzylidene camphor containing a sulphonic function or a benzotriazole silicone of particular formula (1) that will be defined below in detail;

c) at least one dye that is soluble in said medium; said composition not containing an alkyl β,β'-diphenylacrylate compound or alkyl α-cyano-β,β'-diphenylacrylate compound.

This discovery is the basis of the invention.

One subject of the invention is a coloured fragrancing composition comprising, in a cosmetically acceptable medium:

a) at least 2% by weight of a fragrancing substance relative to the total weight of the composition;

b) at least one derivative of benzylidene camphor containing a sulphonic function or a benzotriazole silicone of particular formula (1) that will be defined below in detail;

c) at least one dye that is soluble in said medium; said composition not containing an alkyl β,β'-diphenylacrylate compound or alkyl α-cyano-β,β'-diphenylacrylate compound.

Another subject of the invention is a method for fragrancing human keratin substances and especially the skin, lips, hair, scalp, eyelashes and eyebrows, and nails, or an item of clothing, comprising the application to the keratin substances or said item of clothing of the composition as defined above.

The invention also relates to the use of at least one derivative of benzylidene camphor containing a sulphonic function or a benzotriazole silicone of formula (1), as a stabilizer for the organoleptic properties of a coloured fragrancing cosmetic composition, in particular the colour and/or the odour of said composition, with respect to external attacking factors, especially light or differences in temperature; said composition not containing an alkyl β,β'-diphenylacrylate compound or an alkyl α-cyano-β,β'-diphenylacrylate compound.

The expression "fragrancing composition" is understood to mean any composition that leaves a fragrance after application to keratin substances.

The expression "fragrancing substance" is understood to mean any fragrance or aroma capable of fragrancing the skin and human keratin substances in general including the skin, hair, scalp, lips and nails.

The expression "human keratin substances" is understood to mean the skin (face, body, lips, inside of the eyelids), scalp, hair, eyelashes, eyebrows, nails and mucous membranes.

The expression "cosmetically acceptable medium" in the composition of the invention is understood to mean a non-toxic medium capable of being applied to human keratin substances including the skin, lips, nails, hair, scalp, eyelashes and eyebrows.

The expression "not containing an alkyl β,β'-diphenylacrylate compound or alkyl α-cyano-β,β'-diphenylacrylate compound" is understood to mean containing less than 0.2% by weight of alkyl β,β'-diphenylacrylate or alkyl α-cyano-β,β'-diphenylacrylate compound or even less than 0.1% by weight, or even free of alkyl β,β'-diphenylacrylate compound or of alkyl α-cyano-β,β'-diphenylacrylate compound.

Derivatives of Benzylidene Camphor Containing a Sulphonic Function:

The derivatives of benzylidene camphor containing a sulphonic function are preferably chosen from benzene-1,4-bis(3-methylidene-10-camphorsulphonic) acid (INCI name: Terephthalylidene Dicamphor Sulfonic Acid) and its various salts described especially in patent applications FR-A-2528420 and FR-A-2639347, which are screening agents that are already known per se ("broad band" screening agents), capable specifically of absorbing ultraviolet radiation with wavelengths of between 280 and 400 nm, with absorption maxima of between 320 and 400 nm, in particular about 345 nm.

These screening agents correspond to the general formula (IX) below:

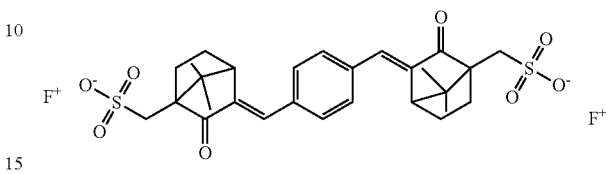

(IX)

in which F denotes a hydrogen atom, an alkali metal or else an $NH(R_3)_3^+$ radical in which the $R_3$ radicals, which may be identical or different, denote a hydrogen atom, a $C_1$-$C_4$ alkyl or hydroxyalkyl radical or else a group $M^{n+}/n$, $M^{n+}$ denoting a multivalent metal cation in which n is equal to 2, 3 or 4, $M^{n+}$ preferably denoting a metal cation chosen from $Ca^{2+}$, $Zn^{2+}$, $Mg^{2+}$, $Al^{3+}$ and $Zr^{4+}$. It is clearly understood that the compounds of formula (I) above can give rise to the "cis-trans" isomer around one or more double bond(s) and that all the isomers fall within the scope of the present invention.

The derivative(s) of benzylidene camphor containing a sulphonic function may be present in the compositions according to the invention at contents ranging from 0.1 to 10%, preferably ranging from 0.1 to 1%, by weight, still with respect to the total weight of the composition.

Silicon Derivatives of Benzotriazole

The silicon derivatives with a benzotriazole function used in the present invention are preferably silanes or siloxanes with a benzotriazole function comprising at least one unit of following formula (1):

$$O_{(3-a)/2}Si(R)_a\text{-}G \quad (1)$$

R represents an optionally halogenated $C_1$-$C_{10}$ alkyl radical or a phenyl radical or a trimethylsilyloxy radical, a is an integer chosen between 0 and 3 inclusive, and the G symbol denotes a monovalent radical bonded directly to a silicon atom which corresponds to the following formula (2):

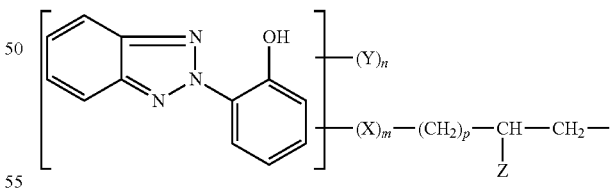

(2)

in which:

Y, which are identical or different, are chosen from $C_1$-$C_8$ alkyl radicals, halogens and $C_1$-$C_4$ alkoxy radicals, it being understood that, in the latter case, two adjacent Y radicals on the same aromatic nucleus can together form an alkylidenedioxy group in which the alkylidene group comprises from 1 to 2 carbon atoms, X represents O or NH, Z represents hydrogen or a $C_1$-$C_4$ alkyl radical, n is an integer between 0 and 3 inclusive, m is 0 or 1, p represents an integer between 1 and 10 inclusive.

These compounds are disclosed in particular in Patent Applications EP-A-0 392 883, EP-A-0 660 701, EP-A-0 708 108, EP-A-0 711 778 and EP-A-711 779.

The silicon derivatives used in the context of the present invention preferably belong to the general family of benzotriazole silicones which is disclosed in particular in EP-A-0 660 701.

A family of benzotriazole silicones which is particularly well suited to the implementation of the present invention is that comprising the compounds corresponding to the following formulae (5) and (6):

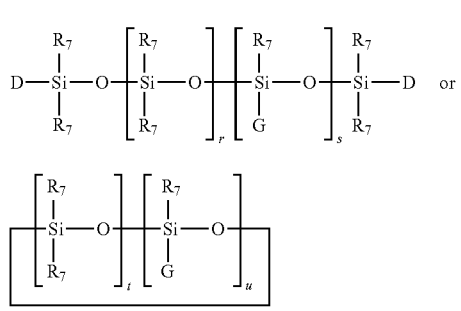

in which
- $R_7$, which are identical or different, are chosen from $C_1$-$C_{10}$ alkyl, phenyl, 3,3,3-trifluoropropyl and trimethylsilyloxy radicals, at least 80% by number of the $R_7$ radicals being methyl,
- D, which are identical or different, are chosen from the $R_7$ radicals and the G radical,
- r is an integer between 0 and 50 inclusive and s is an integer between 0 and 20 inclusive and, if s=0, at least one of the two D symbols denotes G,
- u is an integer between 1 and 6 inclusive and t is an integer between 0 and 10 inclusive, it being understood that t+u is equal to or greater than 3,
- and the G symbol corresponds to the above formula (2).

As emerges from the formula (2) given above, the attachment of the —$(X)_m$—$(CH_2)_p$—CH(Z)—$CH_2$— link to the benzotriazole unit, which therefore ensures that the said benzotriazole unit is connected to the silicon atom of the silicone chain, can, according to the present invention, take place in all the available positions offered by the two aromatic nuclei of the benzotriazole:

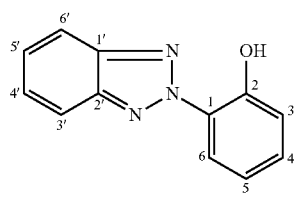

Preferably, this attachment takes place in the 3, 4 or 5 position (aromatic nucleus bearing the hydroxyl functional group) or 4' position (benzene nucleus adjacent to the triazole ring). and more preferably still in the 3, 4 or 5 position. In a preferred embodiment of the invention, the attachment takes place in the 3 position.

Likewise, the attachment of the y substituent unit or units can take place in all the other positions available within the benzotriazole. However, this attachment preferably takes place in the 3, 4, 4', 5 and/or 6 position. In a preferred embodiment of the invention, the attachment of the Y unit takes place in the 5 position.

In the above formulae (5) and (6), the alkyl radicals can be linear or branched and can be chosen in particular from methyl, ethyl, n-propyl, isopropyl, n-butyl, isobutyl, tort-butyl, n-amyl, isoamyl, neopentyl, n-hexyl, n-heptyl, n-octyl, 2-ethylhexyl and tert-octyl radicals. The preferred $R_7$ alkyl radicals according to the invention are the methyl, ethyl, propyl, n-butyl, n-octyl and 2-ethylhexyl radicals.

More preferably still, the $R_7$ radicals are all methyl radicals.

Among the compounds of formulae (5) and (6) above, it is preferable to employ those corresponding to the formula (5), that is to say diorganosiloxanes with a short linear chain.

Among the compounds of formula (5) above, it is preferable to employ those in which the D radicals are both $R_7$ radicals.

Preference is more particularly given, among the linear diorganosiloxanes coming within the scope of the present invention, to statistical derivatives or alternatively block-defined derivatives exhibiting at least one and more preferably still all of the following features:
- D is an $R_7$ radical,
- $R_7$ is alkyl and more preferably still is methyl,
- r is between 0 and 15 inclusive; s is between 1 and 10 inclusive,
- n is non-zero and preferably equal to 1 and Y is then chosen from methyl, tert-butyl or $C_1$-$C_4$ alkoxy,
- Z is hydrogen or methyl,
- m=0 or [m=1 and X═O]
- p is equal to 1.

A family of benzotriazole silicones which is particularly well suited to the invention is that defined by the following general formula (7):

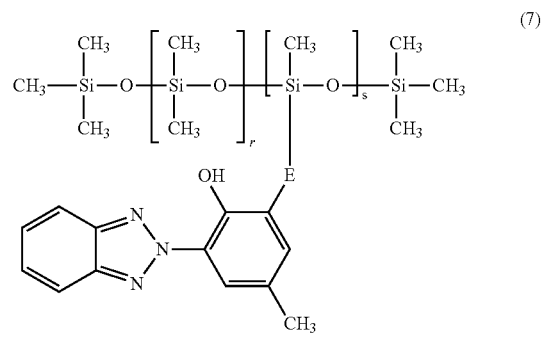

with 0≤r≤10,
1≤s≤10,
and where E represents the divalent radical:

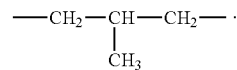

In a particularly preferred embodiment of the invention, the benzotriazole silicone is the compound Drometrizole Trisiloxane (CTFA name) corresponding to the following formula:

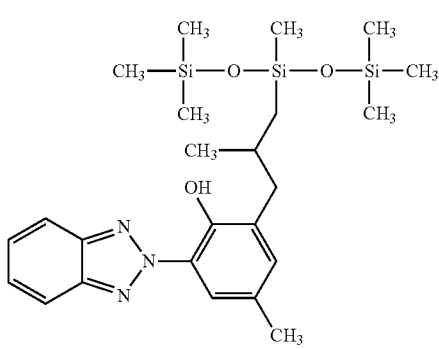 [SMILES: Cc1cc(CC(C)C[Si](C)(O[Si](C)(C)C)O[Si](C)(C)C)c(O)c(-n2nc3ccccc3n2)c1]

Processes suitable for the preparation of the products of formulae (1), (5), (6) and (7) above are disclosed in particular in U.S. Pat. Nos. 3,220,972, 3,697,473, 4,340,709, 4,316,033, and 4,328,346 and in Patent Applications EP-A-0 392 883 and EP-A-0 742 003.

The silicon derivative with a benzotriazole function may be present in the compositions according to the invention at contents ranging from 0.1 to 10%, preferably ranging from 0.1 to 1%, by weight, still with respect to the total weight of the composition.

Fragrancing Substances

Fragrances are compositions containing, in particular, the raw materials described in S. Arctander, Perfume and Flavor Chemicals (Montclair, N.J., 1969) in S. Arctander, Perfume and Flavor Materials of Natural Origin (Elizabeth, N.J., 1960) and in "Flavor and Fragrance Materials—1991", Allured Publishing Co. Wheaton, Ill.

They may be natural products (essential oils, absolutes, resinoids, resins or concretes) and/or synthetic products (terpene or sesquiterpene hydrocarbons, alcohols, phenols, aldehydes, ketones, ethers, acids, esters, nitriles, peroxides, which may be saturated or unsaturated and aliphatic or cyclic).

According to the definition given in the international standard ISO 9235 and adopted by the European Pharmacopoeia Commission, an essential oil is an odorous product generally of complex composition, obtained from a botanically defined plant raw material, either by steam distillation, or by dry distillation, or by a suitable mechanical process without heating (cold expression). The essential oil is usually separated from the aqueous phase by a physical process that does not lead to a significant change in the composition.

Methods of obtaining the essential oils

The choice of the technique depends mainly on the raw material: its original state and its characteristics, its actual nature. The "essential oil/plant raw material" yield may be extremely variable depending on the plants: 15 ppm to more than 20%. This choice conditions the features of the essential oil, in particular viscosity, colour, solubility, volatility, enrichment or depletion in certain constituents.

Steam Distillation

Steam distillation corresponds to the vaporization, in the presence of steam, of a substance that is not very miscible with water. The raw material is brought into contact with water brought to the boil or steam in an alembic. The steam entrains the essential oil vapour which is condensed in the condenser in order to be recovered in the liquid phase in a Florentine flask (or essential jar) where the essential oil is separated from the water by decantation. The aqueous distillate that remains after the steam distillation, once the essential oil has been separated, is referred to as "aromatic water" or "hydrolat" or "floral distilled water".

Dry Distillation

The essential oil is obtained by distillation of the wood, bark or roots, without addition of water or of steam in a sealed chamber designed so that the liquid is recovered in its bottom part. Cade oil is the best known example of this production method.

Cold Expression

This production method is only applied to citrus fruit (Citrus spp.) via mechanical processes at ambient temperature. The principle of the method is the following: the peel is shredded and the content of the intercellular cavities which have been broken is recovered via a physical process. The conventional process consists in carrying out an abrasive action, under a stream of water, over the entire surface of the fruit. After removing the solid waste, the essential oil is separated from the aqueous phase by centrifugation. Most of the industrial installations in fact enable the simultaneous or sequential recovery of the fruit juices and of the essential oil.

Physicochemical Characters

Essential oils are generally volatile and liquid at ambient temperature, which differentiates them from the oils referred to as fixed oils. There are more or less coloured and their density is generally lower than that of water. They have a high refractive index and most deviate polarized light. They are liposoluble and soluble in standard organic solvents, can be distilled with steam and are not very soluble in water.

Among the essential oils that can be used according to the invention, mention may be made of those obtained from plants belonging to the following botanical families:

Abietaceae or Pinaceae: conifers
Amaryllidaceae
Anacardiaceae
Anonaceae: ylang ylang
Apiaceae (for example umbellifers): dill, angelica, coriander, sea fennel, carrot, parsley
Araceae
Aristolochiaceae
Asteraceae: Achillea, artemisia, camomile, Helichrysum
Betulaceae
Brassicaceae
Burseraceae: frankincense
Caryophyllaceae
Canellaceae
Caesalpiniaceae: Copaifera (copaiba)
Chenopodiaceae
Cistaceae: Cistus
Cyperaceae
Dipterocarpaceae
Ericaceae: wintergreen
Euphorbiaceae
Fabaceae
Geraniaceae: geranium
Guttiferae
Hamamelidaceae
Hernandiaceae
Hypericaceae: St. John's wort
Iridaceae
Juglandaceae
Lamiaceae: thyme, oregano, Monarda, savory, basil, marjorams, mints, patchouli, lavenders, sages, catnip, rosemary, hyssop, balm
Lauraceae: Ravensara, bay, rosewood, cinnamon, Litsea
Liliaceae: garlic
Magnoliaceae: magnolia
Malvaceae
Meliaceae Monimiaceae
Moraceae: hemp, hop
Myricaceae
Mysristicacae: nutmeg
Myrtaceae: eucalyptus, tea tree, paperback tree, cajuput, Backhousia, clove, myrtle
Oleaceae
Piperaceae: pepper
Pittosporaceae
Poaceae: citronnella, lemongrass, vetiver
Polygonaceae
Renunculaceae
Rosaceae: roses
Rubiaceae
Rutaceae: the whole citrus family
Salicaceae
Santalaceae: sandalwood
Saxifragaceae
Schisandraceae
Styracaceae: benzoin
Thymelaeaceae: agarwood
Tiliaceae
Valerianaceae: valeriane, nard
Verbenacea: lantana, verbena
Violaceae
Zingiberaceae: galangal, turmeric, cardamom, ginger
Zygophyliaceae Mention may also be made of the essential oils extracted from flowers (lily, lavender, rose, jasmine, ylang ylang, neroli), from stalks and from leaves (patchouli, geranium, bitter orange), from fruit (coriander, aniseed, cumin, juniper), from fruit peel (bergamot, lemon, orange), from roots (angelica, celery, cardamom, iris, sweet flag, ginger), from wood (pine wood, sandalwood, guaiac wood, pink cedar wood, camphorwood), from herbs and from grasses (tarragon, rosemary, basil, lemongrass, sage, thyme), from needles and from branches (spruce, fir, pine, dwarf pine), from resins and from balms (galbanum, elemi, benzoin, myrrh, olibanum or opopanax).

Examples of fragrancing substances are in particular: geraniol, geranyl acetate, farnesol, borneol, bornyl acetate, linalol, linalyl acetate, linalyl propionate, linalyl butyrate, tetrahydrolinalol, citronellol, citronellyl acetate, citronellyi formate, citronellyl propionate, dihydromyrcenol, dihydromyrcenyl acetate, tetrahydromyrcenol, terpineol, terpinyl acetate, nopol, nopyl acetate, nerol, neryl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloro-methylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropyl-phenyl)propanal, 3-(p-tert-butylphenyl)propanal, 2,4-dimethylcyclohex-3-enyl carboxaidehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaidehyde, 4-acetoxy-3-pentyltetrahydropyran, 3-carboxymethyl-2-pentylcyclopentane, 2-n-4-heptvlcyclopentanone, 3-methyl-2-pentyl-2-cyclopentenone, menthone, carvone, tagetone, geranyl acetone, n-decanal, n-dodecanal, 9-decen-1-ol, phenoxvethyl isobutyrate, phenyl acetaldehyde dimethyl acetal, phenylacetaldehyde diethylacetal, geranonitrile, citronellonitrile, cedryl acetate, 3-isocamphylcyclohexanol, cedryl methyl ether, isolongifolanone, aubepinonitrile, aubepin, heliotropin, coumarin, eugenol, vanillin, diphenyl ether, citral, citronellal, hydroxycitronellial, damascone, ionones, methylionones, isomethylionones, solanone, irones, cis-3-hexenol and its esters, indane musks, tetralin musks, isochroman musks, macrocyclic ketones, macrolactone musks, ethylene brassylate and mixtures thereof.

According to one preferred embodiment of the invention, use is made of a mixture of various fragrancing substances that together generate a pleasant note for the user.

Preferably, fragrancing substances will he chosen so that they produce notes (top, heart and base notes) in the following families:
hesperidic notes,
aromatic notes,
floral notes,
spicy notes,
woody notes,
gourmand notes,
chypre notes,
fougere notes,
leather notes, and
musk notes.

The fragrancing compositions of the invention preferably contain from 2% to 40% by weight of fragrancing substance, better still from 2% to 30% by weight, in particular from 2% to 25% by weight relative to the total weight.

The cosmetically acceptable medium in accordance with the present invention preferably contains at least one volatile alcohol and/or one volatile silicone oil and/or one volatile hydrocarbon-based oil and optionally water. Preferentially, the medium of the composition contains water in an amount preferably ranging from 0.01% to 50% and more preferably from 0.5% to 25% by weight relative to the total weight of the composition.

The term "volatile" is understood, within the meaning of the invention, to mean any molecule capable of evaporating on contact with the skin or keratin fibre in less than one hour, at ambient temperature and atmospheric pressure. The volatile compound(s) of the invention are liquid at ambient temperature, have a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

Volatile Alcohols

The expression "volatile alcohol" is understood to mean any compound having at least one hydroxyl group and where more than 95% by weight cf the compound is capable of evaporating in less than one hour at ambient temperature (25° C.) and atmospheric pressure (760 mmHg) in contact with a keratin substance such as the skin or the hair.

The volatile alcohols in accordance with the present invention are preferably chosen from $C_1$-$C_5$ lower monoalcohols and can be chosen from methanol, ethanol, propanol, isopropanol, n-butanol, isobutanol, tert-butanol and more particularly ethanol. Their viscosity at 20° C., measured with a HAAKE Rheostress 600 machine with a rotor that is 60 mm in diameter, an angle of 2° and at a shear rate of 200 $s^{-1}$ is preferably from 0.3 to 3 MPa·s.

The volatile alcohol(s) is (are) preferably present in amounts ranging from 40 to 80% and more preferably in amounts ranging from 55 to 80% by weight relative to the total weight of the composition.

Volatile Silicone Oils

As volatile silicone oils, mention may, for example, be made of volatile linear or cyclic silicone oils, especially those having a viscosity of ≤6 centistokes ($6 \times 10^{-6}$ $m^2$/s), and in particular having from 2 to 10 silicon atoms, these silicones optionally comprising alkyl or alkoxy groups having from 1 to 22 carbon atoms. As a volatile silicone oil that can be used in the invention, mention may especially be made of octamethylcyclotetrasiloxane, decamethvlcyclopenta-siloxane, dodecamethylcyclohexasiloxane, heptamethyl-hexyltrisiloxane, heptamethyloctyltrisiloxane, hexamethyldisiloxane, octamethyltrisiloxane, decamethyltetrasiloxane, dodecamethylpentasiloxane and mixtures thereof.

The volatile silicone oil(s) is (are) preferably present at from 10 to 80% relative to the total weight of the composition.

Volatile Hydrocarbon Oils

The volatile hydrocarbon oils may be chosen from hydrocarbon oils having from 8 to 16 carbon atoms, and in particular $C_8$-$C_{16}$ branched alkanes such as $C_8$-$C_{16}$ isoalkanes of petroleum origin (also known as isoparaffins) such as isododecane (also known as 2,2,4,4,6-pentamethylheptane), isodecane, isohexadecane, the oils sold under the Isopar and Permethyl trade names, branched $C_8$-$C_{16}$ esters, isohexyl neopentanoate, and mixtures thereof. Other volatile hydrocarbon oils such as petroleum distillates, in particular those sold under the name Shell Solt by Shell, may also be used. According to one embodiment, the volatile solvent is chosen from volatile hydrocarbon oils having from 8 to 16 carbon atoms and mixtures thereof.

According to one particularly preferred embodiment of the invention, use will be made, as a hydrocarbon oil, of a volatile linear alkane.

Volatile Linear Alkanes

The composition according to the invention contains one or more volatile linear alkane(s). The expression "one or more volatile linear alkane(s)" is understood to equally mean "one or more volatile linear alkane oil(s)".

A volatile linear alkane suitable for the invention is liquid at ambient temperature (around 25° C.) and at atmospheric pressure (760 mmHg).

The expression "volatile linear alkane", suitable for the invention, is understood to mean a cosmetic linear alkane capable of evaporating on contact with the skin in less than one hour, at ambient temperature (25° C.) and atmospheric pressure (760 mmHg, that is to say 101 325 Pa), that is liquid at ambient temperature, and that has, in particular, an evaporation rate ranging from 0.01 to 15 mg/cm$^2$/min at ambient temperature (25° C.) and atmospheric pressure (760 mmHg).

Preferably, the "volatile linear alkanes" suitable for the invention have an evaporation rate ranging from 0.01 to 3.5 mg/cm$^2$/min at ambient temperature (25° C.) and atmospheric pressure (760 mmHg).

Preferably, the "volatile linear alkanes" suitable for the invention have an evaporation rate ranging from 0.01 to 1.5 mg/cm$^2$/min at ambient temperature (25° C.) and atmospheric pressure (760 mmHg).

More preferably, the "volatile linear alkanes" suitable for the invention have an evaporation rate ranging from 0.01 to 0.8 mg/cm$^2$/min at ambient temperature (25° C.) and atmospheric pressure (760 mmHg).

More preferably, the "volatile linear alkanes" suitable for the invention have an evaporation rate ranging from 0.01 to 0.3 mg/cm$^2$/min at ambient temperature (25° C.) and atmospheric pressure (760 mmHg).

More preferably, the "volatile linear alkanes" suitable for the invention have an evaporation rate ranging from 0.01 to 0.12 mg/cm$^2$/min at ambient. temperature (25° C.) and atmospheric pressure (760 mmHg).

The evaporation rate of a volatile alkane according to the invention (and more generally of a volatile solvent) may especially be evaluated by means of the protocol described in WO 06/013413, and more particularly by means of the protocol described below.

Introduced into a crystallizing dish (diameter: 7 cm), placed on a balance that is located in a chamber of around 0.3 m$^3$, the temperature (25° C.) and hygrometry (50% relative humidity) of which are regulated, are 15 g of volatile hydrocarbon-based solvent.

The liquid is left to evaporate freely, without being stirred, ventilation being provided by a fan (PAPST-MOTOREN, reference 8550 N, rotating at 2700 rpm) placed in a vertical position above-the crystallizing dish containing the volatile hydrocarbon-based solvent, the blades being directed towards the crystallizing dish, at a distance of 20 cm relative to the base of the crystallizing dish.

The mass of volatile hydrocarbon-based solvent remaining in the crystallizing dish is measured at regular time intervals.

The evaporation profile of the solvent is then obtained by plotting the curve of the amount of product evaporated (in mg/cm$^2$) as a function of the time (in min). Then the evaporation rate, which corresponds to the tangent at the origin of the curve obtained, is calculated. The evaporation rates are expressed as mg of volatile solvent: evaporated per unit area (cm$^2$) and per unit time (minutes).

According to one preferred embodiment, the "volatile linear alkanes" suitable for the invention have a non-zero vapour pressure (also known as saturation vapour pressure) at ambient temperature, in particular a vapour pressure ranging from 0.3 Pa to 6000 Pa.

Preferably, the "volatile linear alkanes" suitable for the invention have a vapour pressure ranging from 0.3 to 2000 Pa at ambient temperature (25° C.)

Preferably, the "volatile linear alkanes" suitable for the invention have a vapour pressure ranging from 0.3 to 1000 Pa at ambient temperature (25° C.)

More preferably, the "volatile linear alkanes" suitable for the invention have a vapour pressure ranging from 0.4 to 600 Pa at ambient temperature (25° C.)

Preferably, the "volatile linear alkanes" suitable for the invention have a vapour pressure ranging from 1. to 200 Pa at ambient temperature (25° C.).

More preferably, the "volatile linear alkanes" suitable for the invention have a vapour pressure ranging from 3 to 60 Pa at ambient temperature (25° C.)

According to one embodiment, a linear volatile alkane suitable for the invention may have a flashpoint in the range that varies from 30 to 120° C., and more particularly from 40 to 100° C. The flashpoint is, in particular, measured according to the ISO 3679 standard.

According to one embodiment, an alkane suitable for the invention may be a volatile linear alkane comprising from 7 to 14 carbon atoms.

Preferably, the "volatile linear alkanes" suitable for the invention comprise from 8 to 14 carbon atoms.

Preferably, the "volatile linear alkanes" suitable for the invention comprise from 9 to 14 carbon atoms.

Preferably, the "volatile linear alkanes" suitable for the invention comprise from 10 to 14 carbon atoms.

Preferably, the "volatile linear alkanes" suitable for the invention comprise from 11 to 14 carbon atoms.

According to one advantageous embodiment, the "volatile linear alkanes" suitable for the invention have an evaporation rate, as defined above, ranging from 0.01 to 3.5 mg/cm$^2$/ min at ambient temperature (25° C.) and atmospheric pressure (760 mmHg) and comprise from 8 to 14 carbon atoms.

A volatile linear alkane suitable for the invention may advantageously be of plant origin.

Preferably, the volatile linear alkane or the mixture of volatile linear alkanes present in the composition according to the invention comprises at least one $^{14}C$ isotope of carbon (carbon-14), in particular the $^{14}C$ isotope may be present in a $^{14}C/^{12}C$ ratio greater than or equal to $1 \times 10^{-16}$, preferably greater than or equal to $1 \times 10^{-15}$, more preferably greater than or equal to $7.5 \times 10^{-14}$, and better still greater than or equal to $1.5 \times 10^{-13}$. Preferably, the $^{14}C/^{12}C$ ratio ranges from $6 \times 10^{-13}$ to $1.2 \times 10^{-12}$.

The amount of $^{14}C$ isotopes in the volatile linear alkane or the mixture of volatile linear alkanes may be determined by methods known to a person skilled in the art such as the Libby counting method, liquid scintillation spectrometry or else accelerator mass spectrometry.

Such an alkane may be obtained, directly or in several steps, from a plant raw material such as an oil, a butter, a wax, etc.

As examples of alkanes suitable for the invention, mention may be made of the alkanes described in patent application WO 2007/068371 or WO 2008/155059 by Cognis (mixtures of different alkanes that differ by at least one carbon). These alkanes are obtained from fatty alcohols that are themselves obtained from coconut oil or palm oil.

By way of example of a linear alkane suitable for the invention, mention may be made of n-heptane ($C_7$), n-octane ($C_8$), n-nonane ($C_9$), n-decane ($C_{10}$), n-undecane ($C_{11}$), n-dodecane ($C_{12}$), n-tridecane ($C_{13}$), n-tetradecane ($C_{14}$) and mixtures thereof. According to one particular embodiment, the volatile linear alkane is chosen from n-nonane, n-undecane, n-dodecane, n-tridecane, n-tetradecane, and mixtures thereof.

According to one preferred mode, mention may be made of the mixtures of n-undecane ($C_{11}$) and of n-tridecane ($C_{13}$) obtained in examples 1 and 2 of application WO 2008/155059 by Cognis.

Mention may also be made of n-dodecane ($C_{12}$) and n-tetradecane ($C_{14}$) sold by Sasol respectively under the references PARAFOL 12-97 and PARAFOL 14-97, and also mixtures thereof.

The volatile linear alkane could be used alone.

Alternatively or preferably a mixture of at least two different volatile linear alkanes could be used, that differ from one another by a carbon number n of at least 1, in particular that differ from one another by a carbon number of 1 or 2.

According to a first embodiment, use is made of a mixture of at least two different volatile linear alkanes comprising from 10 to 14 carbon atoms that differ from one another by a carbon number of at least 1. By way of examples, mention may especially be made of the $C_{10}/C_{11}$, $C_{11}/C_{12}$ or $C_{12}/C_{13}$ mixtures of volatile linear alkanes.

According to another embodiment, use is made of a mixture of at least two different volatile linear alkanes comprising from 10 to 14 carbon atoms that differ from one another by a carbon number of at least 2. By way of examples, mention may especially be made of the $C_{10}/C_{12}$ or $C_{12}/C_{14}$ mixtures of volatile linear alkanes, for an even carbon number n and the $C_{11}/C_{13}$ mixture for an odd carbon number n.

According to one preferred mode, use is made of a mixture of at least two different volatile linear alkanes comprising from 10 to 14 carbon atoms that differ from one another by a carbon number of at least 2, and in particular a $C_{11}/C_{13}$ mixture of volatile linear alkanes or a $C_{12}/C_{14}$ mixture of volatile linear alkanes.

Other mixtures combining more than 2 volatile linear alkanes according to the invention, such as for example a mixture of at least 3 different volatile linear alkanes comprising from 7 to 14 carbon atoms that differ from one another by a carbon number of at least 1, are also part of the invention, but the mixtures with 2 volatile linear alkanes according to the invention are preferred (binary mixtures), said 2 volatile linear alkanes preferably representing more than 95% and better sta.1.1 more than 99% by weight of the total content of volatile linear alkanes in the mixture. According to one particular mode of the invention, in a mixture of volatile linear alkanes, the volatile linear alkane having the smallest carbon number is predominant in the mixture.

According to another mode of the invention, use is made of a mixture of volatile linear alkanes in which the volatile linear alkane having the highest carbon number is predominant in the mixture.

By way of examples of mixtures suitable for the invention, mention may especially be made of the following mixtures:

from 50 to 90% by weight, preferably from 55 to 80% by weight, more preferably from 60 to 75% by weight of $C_n$ volatile linear alkane with n ranging from 7 to 14;

from 10 to 50% by weight, preferably from 20 to 45% by weight, preferably from 24 to 40% by weight. of volatile linear alkane with x greater than or equal to 1, preferably x=1 or x=2, with n+x between 10 and 14, relative to the total weight of alkanes in said mixture.

In particular, said mixture of alkanes according to the invention contains:

less than 2% by weight, preferably less than 1% by weight, of branched hydrocarbons;

and/or less than 2% by weight, preferably less than 1% by weight, of aromatic hydrocarbons;

and/or less than 2% by weight, preferably less than 1% by weight and preferentially less than 0.1% by weight, of unsaturated hydrocarbons in the mixture.

More particularly, a volatile linear alkane suitable for the invention may be used in the form of an n-undecane/n-tridecane mixture.

In particular, use will be made of a mixture cif volatile linear alkanes comprising:

from 55 to 80% by weight, preferably from 60 to 75% by weight, of $C_{11}$ (n-undecane) volatile linear alkane;

from 20 to 45% by weight, preferably from 24 to 40% by weight, of $C_{13}$ (n-tridecane) volatile linear alkane relative to the total weight of alkanes in said mixture.

According to one particular embodiment, the mixture of alkanes is an n-undecane/n-tridecane mixture. In particular, such a mixture may be obtained according to Example 1 or Example 2 of WO 2008/155059.

According to another particular embodiment, use is made of the n-dodecane sold under the reference PARAFOL 12-97 by Sasol.

According to another particular embodiment, use is made of the n-tetradecane sold under the reference PARAFOL 14-97 by Sasol.

According to yet another embodiment, use is made of a mixture of n-dodecane and of n-tetradecane.

Additives

The composition of the invention may also comprise any additive usually used in the field of fragrances chosen especially from antioxidants, fatty substances such as oils (plant, mineral or synthetic oils such as esters, perfluoroethers), cosmetic or dermatological active agents such as, for example, emollients or demulcents such as sweet almond oil, apricot kernel oil, hydrating agents such as glycerol, soothing agents such as α-bisabolol, allantoin, aloe vera; vitamins and derivatives thereof, essential fatty acids, insect repellents, propellants, peptizing agents, fillers, co-solvents, UV screening agents other than hydrophilic UVA screening agents, stabilizers or preservatives, dyes, pearlescent agents, glitter flakes and mixtures thereof. When they are present in the composition of the invention, these additives may be present in an amount ranging from 0.01 to 10% and better still from 0.01% to 5% by weight relative to the total weight of the composition.

Among the co-solvents that can be used according to the invention, mention may be made of octyldodecanol, triethyl citrate, dicaprylyl carbonate, isononyl isononanoate, isopropyl myristate, isopropyl palmitate, and 2-ethylhexyl palmitate.

Among the additional UV screening agents, mention may be made of organic screening agents that screen out UVA and/or UVB radiation such as:
  dibenzoylmethane derivatives such as butyl methoxydibenzoylmethane sold in particular under the trade name PARSOL 1789 by DSM Nutritional Products,
  hydrophilic benzophenone derivatives such as benzophenone-3 or oxygenzone sold under the trade name UVINUL M40 by BASF,
  aminobenzophenone derivatives such as n-hexyl 2-(4-diethylamino-2-hydroxybenzoyl)benzoate sold under the trade name UVINUL A+ by BASF,
  salicylic acid derivatives such as homosalate sold under the trade name EUSOLEX HMS by Rona/EM Industries and ethylhexyl salicylate sold under the name NEO HELIOPAN OS by Symrise,
  cinnamic acid derivatives such as ethyihexyl methoxycinnamate sold in particular under the trade name PARSOL MCX by DSM Nutritional Products.

The composition of the invention may also comprise dyes soluble in the carrier of said composition.

As soluble dyes in accordance with the invention, mention may be made of the water-soluble or hydrophilic dyes such as:
  caramel, Yellow 5, Acid Blue 9/Blue 1, Green 5, Green 3 /Fast Green FCF 3, Orange 4, Red 4 /Food Red 1, Yellow 6, Acid Red 33 /Food Red 12, Red 40, cochineal carmine (CI 15850, CI 75470), Ext. Violet 2, Red 6-7, Ferric Ferrocyanide, Ultramarines, Acid Yellow 3/Yellow 10, Acid Blue 3, Yellow 10.

The soluble dye(s) in accordance with the invention are preferably present in amounts ranging from $10^{-5}$ to 1% of the total weight of the composition, preferably from $10^{-4}$ to 0.1% of the total weight of the composition.

As colour stabilizers for fragrances, mention will be made of tris(tetramethylhydroxypiperidinol) citrate such as the product sold under the name TINOGUARD Q by Ciba-Geigy, sodium benzotriazolyl butylphenol sulphonate such as the product sold under the name TINOGUARD HS by Ciba-Geigy; benzotriazolyl dodecyl p-cresol such as the product sold under the name TINOGUARD TL by Ciba-Geigy, such as the product sold under the trade name CIBAFAST H LIQUID by Ciba-Geigy. Bumetrizole such as the product sold under the name TINOGUARD AS by Ciba-Geigy.

According to one particular form of the invention, use will also be made of at least one antioxidant and/or at least one peptizer so as to improve the clarity of the composition and/or to reduce or even eliminate the low-temperature precipitation phenomena which may be caused by certain fragrances and/or to improve the stability of the composition during storage.

Among the antioxidants, mention may be made, for example, of BHA (tert-butyl-4-hydroxyanisole), BHT (2,6-di-tert-butyl-p-cresol), tocopherols such as vitamin E and its derivatives such as tocopheryl acetate. They are used at concentrations ranging from 0.01% to 1% relative to the total weight of the composition.

Among the peptizers that can be used according to the invention, Use will more particularly be made of hydrogenated castor oil that is oxyethylenated with 60 mol of ethylene oxide: INCI name: PEG-60 Hydrogenated Castor Oil such as the products sold under the trade names CREMOPHOR RH60 or CREMOPHOR C040 by BASF. They are used at concentrations ranging from 0.1% to twice the concentration of fragrance concentrate relative to the total weight of the composition.

Of course, a person skilled in the art will be sure to choose the optional additional additives and/or their amount in such a way that the advantageous properties of the composition according to the invention are not, or not substantially, impaired by the envisaged addition.

Galenic Forms

The invention applies not only to the fragrancing products but also to care products and products for treating the skin, including the scalp, and the lips, that contain an odorous substance. The composition according to the invention may thus constitute fragrancing, care or treatment composition for keratin substances, and especially may be in the form of eau fraiche (splash), eau de toilette, eau de parfum, after-shave lotion, skin care water, silicon-based or hydrbsilicone-based care oil. It may also be in the form of a fragranced two-phase lotion (eau de toilette phase/hydrocarbon oil and/or silicone oil phase).

The composition according to the invention may be manufactured by known processes, generally used in the field of fragranced formulations.

The compositions according to the invention may be packaged in the form of bottles.

The fragrancing composition of the invention may be dispersed according to various systems such as sprays, aerosols and piezoelectric devices.

They may also be applied in the form of fine particles by means of mechanical pressurization or propellant gas devices. The devices according to the invention are well known to a person skilled in the art and comprise pump bottles or sprays, aerosol containers comprising a propellant and also aerosol pumps that use compressed air as a propellant. The latter are described in patents U.S. Pat. Nos. 4,077,441 and 4,850,517.

The compositions packaged in an aerosol in accordance with the invention generally contain conventional propellants such as, for example, dimethyl ether, isobutane, n-butane and propane.

The fragrancing compositions are preferably transparent. Their transparency is measured by a turbidity ranging from 1 to 200 NTU and preferably from 10 to 90 NTU, the turbidity being measured at 24 hours using a Hach Model 2100 P portable turbidimeter.

The compositions according to the invention are, according to one particular form of the invention, lotions and preferably have a viscosity ranging from 10 to 120 DU and more preferably from 30 to 120 DU, more preferably still from 40 to 80 DU; the viscosity being measured using a Rheomat TVe-05, at 25° C., with a speed of rotation of 200 rpm, spindle No. 1, 10 min. These low viscosities make it possible to package the compositions of the invention using mechanical pressurization or propellant gas devices so as to be applied in the form of fine particles (vaporization).

The invention will now be described with reference to the following examples given by way of illustration and non-limitingly. In these examples, unless indicated otherwise, the amounts are expressed as weight percentages. The following fragranced formulations were produced; the amounts are indicated as percentages by weight:

EXAMPLES

The tests were carried out according to the measurement protocol described in EP 1 897 592 A1, but on various colours, in order to demonstrate the protective power of each of the following screening agents:
(1) the sulphonic benzylidene camphor derivative: Terephthalylidene dicamphor sulphonic acid (MEXORYL SX)
(2) the benzotriazole silicone of formula (1): Drometriazole trisiloxane (MEXORYL XL) on two types of very different colours:
YELLOW 5/CI 19140
EXT. VIOLET 2/CI 60730
Principle The principle of these tests consists in exposing the products to be tested to an irradiating light source the spectral distribution of which is perfectly defined and the energy emitted perfectly quantified. The light sources commonly used are xenon lamps that emit through:
  a platinum-coated quartz filter which deflects infrared radiation and eliminates it via the top of the device; and
  a glass filter, which by absorbing short ultraviolet radiation, makes it possible to simulate the radiation received behind a display window.
Equipment
A CPS Sun—test machine is used:
  The illumination provided by a xenon lamp between 300 and 800 nm is set at 765 W/m$^2$ (value set by the manufacturer);
  the optical filtration is provided by a quartz filter with an IR coating and special glazing glass).

The colour of each bottle before and after exposure to light is then observed with the naked eye and using a Minolta CM3600-d spectrophotometer. The colour obtained is quantified. The results, in the form of averages, are expressed in the (L*, a*, b*) system in which L* represents the lightness, a* represents the red-green axis (−a*=green, +a*=red) and b* represents the yellow-blue axis (−b*=blue, +b*=yellow). Thus, a* and b* express the colour of the composition. The variation in colour of the eau de toilette after 16 h of sun test is evaluated by eye, but also by the spectrocolorimeter, via the ΔE, which corresponds to the square root of the sum of the squares of the L* a* b* values of the spectrocolorimeter. The higher the value of ΔE, the greater the degradation of the colour.

The following formulations are produced and tested:

| Ingredients | Ex 1 (outside the invention) | Ex 2 (outside the invention) | Ex 3 (outside the invention) | Ex 4 (invention) |
|---|---|---|---|---|
| Fragrance OTB Flanker | 10.00 | 10.00 | 10.00 | 10.00 |
| Dye | X | X | X | X |
| Octocrylene (UVINUL N539) | — | 0.20 | 0.20 | — |
| Butyl methoxydibenzoyl-methane (PARSOL 1789) | — | 0.20 | — | — |
| Terephthalylidene dicamphor sulphonic acid (MEXORYL SX) | — | — | 0.20 as active material | 0.40 as active material |
| Ethanol | 75.00 | 75.00 | 75.00 | 75.00 |
| Water | qs for 100 | qs for 100 | qs for 100 | qs for 100 |

| Ingredients | Ex 5 (outside the invention) | Ex 6 (outside the invention) | Ex 7 (outside the invention) | Ex 8 (invention) |
|---|---|---|---|---|
| Fragrance OTB Flanker | 10.00 | 10.00 | 10.00 | 10.00 |
| Dye | X | X | X | X |
| Octocrylene (UVINUL N539) | — | 0.20 | 0.20 | — |
| Butyl methoxydibenzoyl-methane (PARSOL 1789) | — | 0.20 | — | — |
| Drometrizole trisiloxane (MEXORYL XL) | — | — | 0.20 | 0.40 |
| Ethanol | 75.00 | 75.00 | 75.00 | 75.00 |
| Water | qs for 100 | qs for 100 | qs for 100 | qs for 100 |

The dyes are used in the following amounts X:
YELLOW 5/CI 19140 5.25 ppm
EXT. VIOLET 2/CI 60730 1.75 ppm
The results obtained are the following:

TABLE 1

| Dye | Ex 1 (outside the invention) | Ex 2 (outside the invention) | Ex 3 (outside the invention) | Ex 4 (invention) |
|---|---|---|---|---|
| Yellow dye | ΔE = 16.6 (discoloured) | ΔE = 10.2 (Yellow) | ΔE = 12.4 (discoloured) | ΔE = 9.4 (Yellow) |
| Violet dye | ΔE = 5.2 (discoloured) | ΔE = 2.3 (discoloured) | ΔE = 1.8 (discoloured) | ΔE = 0.5 (Violet) |

It is observed that composition 4 according to the invention comprising the sulphonic benzylidene camphor derivative screening agent alone without an alkyl β,β'-diphenylacrylate compound or an alkyl α-cyano-β,β'-diphenylacrylate compound (i.e. octocrylene) has a colour which is more stable over time than
  composition 1 without screening agent;
  composition 2 that combines octocrylene with another UVA screening agent: butyl methoxy-dibenzoylmethane (PARSOL 1789);
  composition 3 that combines octocrylene with a hydrophilic UVA screening agent: terephthalylidene dioamehor sulphonic acid (MEXORYL SX).

TABLE 2

| Dye | Ex 5 (outside the invention) | Ex 6 (outside the invention) | Ex 7 (outside the invention) | Ex 8 (invention) |
|---|---|---|---|---|
| Yellow dye | ΔE = 16.6 (discoloured) | ΔE = 10.2 (Yellow) | ΔE = 10.4 (Yellow) | ΔE = 4.48 (Yellow) |
| Violet dye | ΔE = 5.2 (discoloured) | ΔE = 2.3 (discoloured) | ΔE = 1.8 (discoloured) | ΔE = 0.5 (Violet) |

It is observed that composition 8 according to the invention comprising the benzotriazole silicone screening agent of formula (1) (i.e. drometrizole trisiloxane) without an alkyl β,β'-diphenylacrylate compound or an alkyl α-cyano-β,β'-diphenylacrylate compound (i.e. octocrylene) has a colour which is more stable over time than
  composition 5 without screening agent;
  composition 6 that combines octocrylene with another UVA screening agent;
  composition 7 that combines octocrylene with the benzotriazole silicone of formula (1): drometrizole trisiloxane.

It is deduced therefrom that the presence of octocrylene has a tendency to inhibit the colour photoprotective effect of the sulphonic benzylidene camphor derivative or of the benzotriazole silicone of formula (1) on the colour of the fragrance.

The invention claimed is:

1. Coloured fragrancing composition comprising, in a cosmetically acceptable medium:
  a) at least 2% by weight of a fragrancing substance relative to the total weight of the composition;
  b) at least one derivative of benzylidene camphor with a sulphonic function which is benzene-1,4-di(3-methylidene-10-camphorsulphonic) acid, and/or one of its salts and their isomeric forms of formula (IX) below:

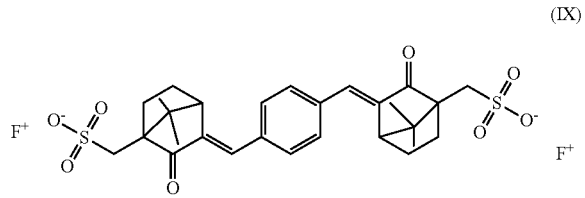

(IX)

in which F denotes a hydrogen atom, an alkali metal or an $NH(R_3)_3^+$ radical in which the $R_3$ radicals, which may be identical or different, denote a hydrogen atom, a $C_1$-$C_4$ alkyl or hydroxyalkyl radical or a group $M^{n+}/n$, $M^{n+}$ denoting a multivalent metal cation in which n is equal to 2, 3 or 4,
or a benzotriazole silicone of following formula (7):

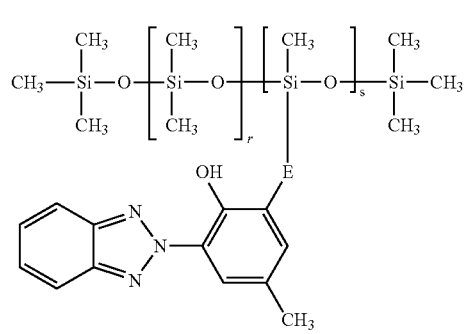

(7)

with 0≤r≤10,
  1≤s≤10,
and where E represents the divalent radical:

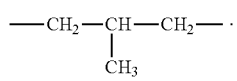

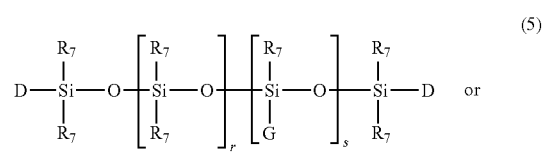

(5)

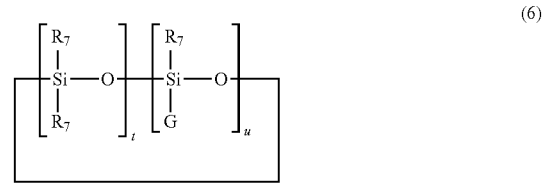

(6)

c) at least one dye that is soluble in said medium; said composition not containing an alkyl β,β'-diphenylacrylate or alkyl α-cyano-β,β'-diphenylacrylate compound; and whereby said composition has improved stability of colour and organoleptic properties due to the at least one derivative of benzylidene camphor or benzotriazole silicone.

2. Composition according to claim 1, wherein b) contains the derivative of benzylidene camphor is benzene-1,4-di(3-methylidene-10-camphorsulphonic) acid and/or one of its various salts.

3. Composition according to claim 1, where the compound of formula (7) is the drometrizole trisiloxane compound corresponding to the following formula:

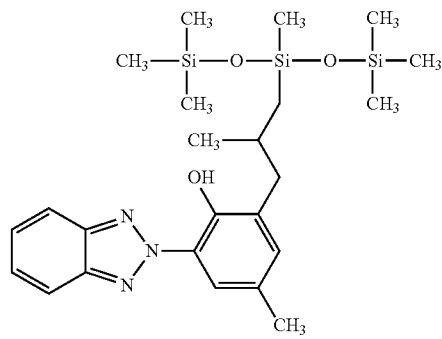 [SMILES: Cc1cc(CC(C)C[Si](C)(O[Si](C)(C)C)O[Si](C)(C)C)c(O)c(-n2nc3ccccc3n2)c1]

4. Composition according to any one of claim 1, comprising, in addition, at least one additive chosen from antioxidants, fatty substances, cosmetic active agents, dermatological active agents, vitamins and derivatives thereof, essential fatty acids, insect repellents, propellants, peptizing agents, fillers, co-solvents, UV screening agents other than those of formula (1), stabilizers or preservatives, dyes, pearlescent agents, glitter flakes and mixtures thereof.

5. Composition according to claim 1, in the form of an eau fraiche (splash), eau de toilette, eau de parfum, aftershave lotion, care water, silicone-based or hydrosilicone-based care oil or fragranced two-phase lotion.

6. Composition according to claim 1, packaged in the form of a bottle; packaged in pressurized form in a spray, or an aerosol, or a piezoelectric device.

7. Method for fragrancing human keratin substances or clothing, comprising the application to said keratin substances or said clothing of the composition as defined in claim 1.

8. Composition according to claim 1, which comprises a) 2%-40% by weight of said fragrancing substance relative to the total weight of the composition; (b) 0.1 to 1% by weight of said at least one derivative of benzylidene camphor with a sulphonic function or said benzotriazole silicone; and (c) $10^{-4}$ to 0.1% by weight of said at least one dye relative to the total weight of the composition.

9. Composition according to claim 8, wherein (b) contains a the derivative of b enzylidene camphor is benzene-1,4-di (3-methylidene-10-camphorsulphonic) acid and/or one of its various salts.

10. Composition according to claim 1, which comprises (b) 0.1 to 10% by weight of said at least one derivative of benzylidene camphor with a sulphonic function or said benzotriazole silicone.

11. Composition according to claim 10, which comprises $10^{-5}$ to 1% by weight of said at least one dye relative to the total weight of the composition.

12. Composition according to claim 1, which comprises $10^{-5}$ to 1% by weight of said at least one dye relative to the total weight of the composition.

13. Composition according to claim 1, which comprises at least one benzene-1,4-di(3-methylidene-10-camphorsulphonic) acid, and/or salt thereof and isomeric forms thereof of formula (IX), wherein $M^{n+}$ denotes a metal cation chosen from $Ca^{2+}$, $Zn^{2+}$, $Mg^{2+}$, $Ba^{2+}$, $Al^{3+}$ and $Zr^{4+}$.

* * * * *